(12) United States Patent
Appella et al.

(10) Patent No.: US 9,156,778 B2
(45) Date of Patent: Oct. 13, 2015

(54) CROSS-COUPLED PEPTIDE NUCLEIC ACIDS FOR DETECTION OF NUCLEIC ACIDS OF PATHOGENS

(75) Inventors: Daniel H. Appella, Rockville, MD (US); Christopher Micklitsch, Rockville, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 17 days.

(21) Appl. No.: 13/592,490

(22) Filed: Aug. 23, 2012

(65) Prior Publication Data

US 2012/0322053 A1 Dec. 20, 2012

Related U.S. Application Data

(63) Continuation of application No. 12/409,159, filed on Mar. 23, 2009, now abandoned, which is a continuation-in-part of application No. 12/441,925, filed as application No. PCT/US2007/020466 on Sep. 21, 2007, now abandoned.

(60) Provisional application No. 60/846,354, filed on Sep. 22, 2006, provisional application No. 60/896,667, filed on Mar. 23, 2007.

(51) Int. Cl.
  *C12Q 1/70* (2006.01)
  *C07C 271/24* (2006.01)
  *C07C 303/40* (2006.01)
  *C07K 14/00* (2006.01)

(52) U.S. Cl.
  CPC .............. *C07C 271/24* (2013.01); *C07C 303/40* (2013.01); *C07K 14/003* (2013.01); *C07B 2200/07* (2013.01); *C07C 2101/08* (2013.01); *Y10T 436/143333* (2015.01)

(58) Field of Classification Search
  CPC ........................... C12Q 1/6883; C07K 14/003
  See application file for complete search history.

(56) References Cited

U.S. PATENT DOCUMENTS 5,969,128 A * 10/1999 De Vos et al. ................. 536/25.3
6,110,676 A * 8/2000 Coull et al. .................. 435/6.18

(Continued)

FOREIGN PATENT DOCUMENTS

WO  WO 2008/039367 A1  4/2008

OTHER PUBLICATIONS

Prescott et al "USe of PNA oligonucleotides for the in situ detection or *Escherichia coli* in water" Molecular and cellular Probes, 1999, 13: 261-268.*

(Continued)

*Primary Examiner* — Betty Forman
(74) *Attorney, Agent, or Firm* — Leydig, Voit & Mayer, Ltd.

(57) ABSTRACT

Disclosed is a method for lowering the detection limit in a method of detecting a nucleic acid comprising (i) contacting a solution comprising a first PNA with a substrate having a second PNA affixed thereto, the second PNA comprising at least one trans-cyclopentane residue, wherein the first PNA has two linker-attached biotins attached thereto and the first and second PNAs being complementary to different portions of a target DNA; (ii) contacting a sample suspected of containing the nucleic acid with the first and second PNAs; and (iii) determining the presence of the reporter molecule on the substrate. Also disclosed are a detection assay and a kit for detecting a target nucleic acid.

17 Claims, 7 Drawing Sheets

(56) References Cited

U.S. PATENT DOCUMENTS

| | | |
|---|---|---|
| 6,596,489 B2 | 7/2003 | Dattagupta et al. |
| 2003/0077608 A1 | 4/2003 | Coull et al. |
| 2003/0232402 A1 | 12/2003 | Stender et al. |
| 2004/0072158 A1* | 4/2004 | Henkens et al. ............... 435/6 |

OTHER PUBLICATIONS

Zecchini et al "Detection of nucleic acids in the attomole range using polybiotinylated oligonucleotide probes" Biotechniques, 1995, 19(2): 286-290.*

Daly and Gilheany, "The synthesis and use in asymmetric epoxidation of metal salen complexes derived from enantiopure *trans*-cyclopentane- and cyclobutane-1,2-diamine," Tetrahedron: Asymmetry, Jan. 2003, 14(1), 127-137.

Edwards, K.A. et al., "*Bacillus anthracis*: toxicology, epidemiology and current rapid-detection methods," Anal. Bioanal. Chem., Jan. 2006, 384(1), 73-84.

Gouin et al., "Synthesis of two stereoisomeric polydentate ligands, *trans* and *cis* cyclopentane-1,2-diaminotetraacetic acids, and complexation by $^{111}$In and $^{153}$Sm," Tetrahedron, Feb. 2002, 58(6), 1131-1136.

Green et al., "Demonstration of a capsule plasmid in *Bacillus anthracis*," Infect. Immun., Aug. 1985, 49(2), 291-297.

Jie Wu et al., "Effective Ring-Opening Reaction of Aziridines with Trimethylsilyl Compounds: A Facile Access to beta-Amino Acids and 1,2-Diamine Derivatives" Journal of Organic Chemistry., Mar. 2000, 65(5), 1344-1348.

Kotti et al., "Vicinal diamino functionalities as privileged structural elements in biologically active compounds and exploitation of their synthetic chemistry" Chem. Bio. Drug Des., Feb. 2006, 67(2), 101-114.

Larrow and Jacobson, "Asymmetric Processes Catalyzed by Chiral (Salen)Metal Complexes," Organomet. Chem., 2004, 6, 123-152.

Lucet et al., "The Chemistry of Vicinal Diamines," Angew Chem., Int. Ed., Oct. 1998, 37(19), 2580-2627.

Luna et al., "Biocatalytic approaches toward the synthesis of both enantiomers of transcyclopentane-1,2-diamine" Org. Lett., Oct. 2002, 4(21), 3627-3629.

Myers et al., "A Cyclopentane Conformational Restraint for a Peptide Nucleic Acid: Design, Asymmetric Synthesis, and Improved Binding Affinity to DNA and RNA," Org. Lett., Jul. 2003, 5(15), 2695-2698.

Ongeri et al., "A Short Synthesis of *trans*-Cyclopentane-1,2-Diamine," Synth. Commun., Jul. 2000, 30, 2593-2597.

Pokorski et al., "(S,S)-trans-Cyclopentane-constrained peptide nucleic acids: A general backbone modification that improves binding affinity and sequence specificity," J. Am. Chem. Soc., Nov. 2004, 126(46), 15067-15073.

Pokorski, J.K. et al., "Cyclopentane-modified PNA improves the sensitivity of nanoparticle-based scanometric DNA detection," Chemical Communications (Cambridge, England), Apr. 2005, 16, 2101-2103.

Pomerantsev et al., "Genome engineering in *Bacillus anthracis* using Cre recombinase," Infect. Immun., Jan. 2006, 74(1), 682-693.

Qun Xu et al., "Practical Synthesis of trans-tert-Butyl-2-aminocyclopentylcarbama te and Resolution of Enantiomers" Journal of Organic Chemistry., Oct. 2006, 71(22), 8655-8657.

Toftlund and Pedersen, "The Preparation and Optical Activity of the Isomers of the 1,2-Cyclopentanediamine Cobalt (III) and Chromium (III)," Acta Chem. Scand., 1972, 26, 4019-4030.

Williams et al., "Foye's Principles of Medicinal Chemistry," 2002, 5th ed., p. 50.

Yoon and Jacobsen, "Privileged Chiral Catalysts," Science, Mar. 2003, 299(5613), 1691-1693.

* cited by examiner (+PA)    (-PA)

Visual signal from 2.5 µg anthrax DNA.

FIG. 3

Represents the first PNA, having a first cross-reactive functional group and a reporter molecule.

Represents the second PNA, having a second cross-reactive functional group, that is attached to the substrate.

Represents the nucleic acid of the sample.

Synthetic Target DNA: 5'-GGA-TTA-TTG-TTA-TAG-GAA-TAG-TTA-AAT-3'
Surface Probe (SP1): H$_2$N CO-Lys-(mPEG-Cys-Ac)-TTA-TAA-CTA-TTC-CTA-mPEG$_2$-Ac
Reporter Probe (RP1): H$_2$N CO-Lys-(mPEG-Ac)-CCT-AAT-AAC-AAT-mPEG$_3$-Mal
ESI-MS [M+Na]+ , calc'd - 8859.7 , obs'd - 8860.0

CROSS-COUPLED PEPTIDE NUCLEIC ACIDS FOR DETECTION OF NUCLEIC ACIDS OF PATHOGENS

CROSS REFERENCE TO RELATED APPLICATION

This application is a continuation of U.S. patent application Ser. No. 12/409,159, filed Mar. 23, 2009, which is a continuation in part of U.S. patent application Ser. No. 12/441,925 filed Dec. 10, 2009, which claims benefit to International Patent Application No. PCT/US2007/020466, filed Sep. 21, 2007, which claims benefit of U.S. Provisional Application Nos. 60/846,354, filed Sep. 22, 2006 and 60/896,667, filed Mar. 23, 2007. The disclosures of each of the foregoing are incorporated herein by reference in their entirety.

TECHNICAL FIELD

The instant invention concerns methods for detecting nucleic acids.

BACKGROUND

Polymerase chain reaction (PCR) is a widely used technique for the detection of pathogens. The technique uses a DNA polymerase used to amplify a piece of DNA by in vitro enzymatic replication. The PCR process generates DNA that is used as a template for replication. This results in a chain reaction that exponentially amplifies the DNA template.

Technologies for genomic detection most commonly use DNA probes to hybridize to target sequences. To achieve required sensitivity, the use of PCR to amplify target sequences has remained standard practice in many labs. While PCR has been the principle method to identify genes associated with disease states, the method has remained confined to use within a laboratory environment. Most current diagnostic applications that can be used outside of the laboratory are based on antibody recognition of protein targets and use ELISA-based technologies to signal the presence of a disease. These methods are fast and fairly robust, but they can lack the specificity associated with nucleic acid detection.

Recently, it was reported that incorporating trans-1,2-diaminocyclopentane into aminoethylglycine peptide nucleic acids (aegPNAs) significantly increases binding affinity and sequence specificity to complementary DNA. See, Pokorski, et al, *J. Am. Chem. Soc.* 2004, 126, 15067-15073 and Myers, et al, *Org. Lett.* 2003, 5, 2695-2698. Despite the promise of PNAs with 1,2-diaminocyclopentane residues in the backbone, commercially viable uses of such PNAs have not been realized.

There is a need for pathogen detection methods that are highly specific and robust for use outside of a laboratory environment.

SUMMARY

In some aspects, the invention concerns methods of detecting a nucleic acid comprising:

contacting a solution comprising a first PNA having a first cross-reactive functional group with a substrate having a second PNA affixed thereto, said second PNA having a second first cross-reactive functional group, wherein the first PNA has a reporter molecule attached thereto and the first and second PNAs being complementary to different portions of a target DNA;

contacting a sample suspected of containing the nucleic acid with said first and second PNAs;

determining the presence of said reporter molecule on said substrate. The substrate can be washed prior to determining the presence of said reporter molecule.

In some aspects, the substrate is visually observed to detect the appearance of color from the reporter molecule. The detecting can be performed visually by an observer.

Preferred PNAs for the first and second PNAs include trans-cyclopentane-containing PNAs.

Any suitable cross-reactive functional groups may be used. For example, pyrrole-2,5-dione and a thiol functionality can be used as the functional groups. In some embodiments, the first cross-reactive group comprises a pyrrole-2,5-dione functionality. In certain embodiments, the second cross-reactive group comprises a thiol functionality. In addition, in some preferred embodiments, the reporter molecule is biotin.

While the instant methods can be used to detect a wide variety of samples, particularly useful samples include anthrax, avian flu, severe acute respiratory syndrome (SARS), tuberculosis (TB), human papilloma virus (HPV), or human immunodeficiency virus (HIV).

In one aspect, the invention concerns methods where the detection is performed by a method comprising:

contacting a solution comprising a first PNA with a substrate having a second PNA affixed thereto, wherein the PNA has a reporter molecule attached thereto and the first and second trans-cyclopentane PNAs being complementary to different portions of a target DNA;

contacting DNA with the first and second cyclopentane-containing PNAs;

visually observing the substrate to detect the appearance of color from the reporter molecule.

The invention also concerns kits for detecting a nucleic acid comprising:

solution comprising a first PNA having a first cross-reactive functional group; and a substrate having a second PNA affixed thereto, said second PNA having a second first cross-reactive functional group, wherein the first PNA has a reporter molecule attached thereto and the first and second PNAs being complementary to different portions of a target DNA;

Some kits may be adapted for detecting an infectious agent such as anthrax, avian flu, severe acute respiratory syndrome (SARS), tuberculosis (TB), human papilloma virus (HPV), or human immunodeficiency virus (HIV).

In yet other embodiments, the kit further comprises biotin-labeled PNA detection probe, such as an avidin-horseradish peroxidase conjugate.

BRIEF DESCRIPTION OF THE DRAWINGS

FIG. 3 shows colorimetric detection of protective antigen DNA (PA) from *Bacillus anthracis* Ames 35 strain (+PA) and Ames 33 strain (−PA). The signal is obtained from PNA-based sandwich-hybridization using PNAα(2) and (2) with poly-HRP-avidin.

DETAILED DESCRIPTION OF ILLUSTRATIVE EMBODIMENTS

Figure 1:
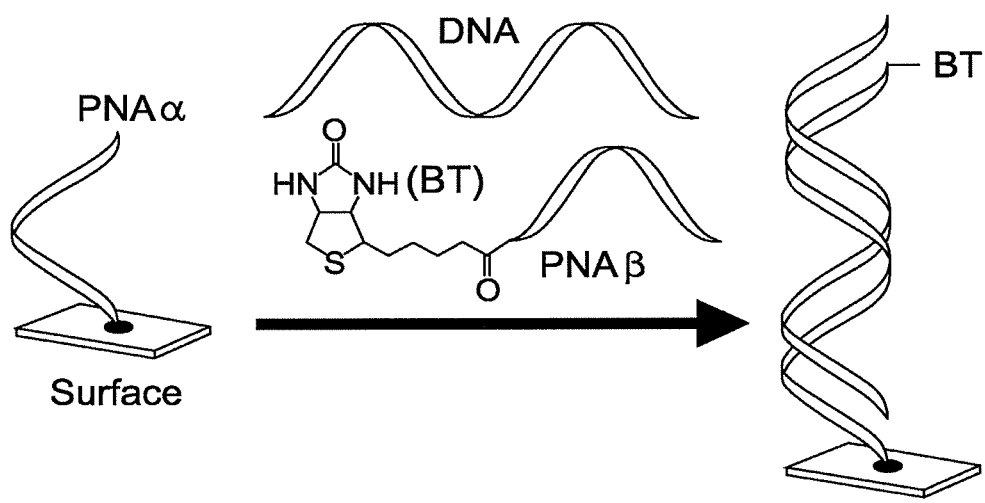
FIG. 1 shows a PNA-based sandwich-hybridization assay. PNAα is the capture probe, and PNAβ is the detection probe.

The present invention concerns diagnostic methods for detection of nucleic acids, without using PCR, that also is very stable. Using peptide nucleic acids (PNAs) we have engineered a system in which two PNAs with cross-reactive functional groups target adjacent sites of an oligonucleotide sequence associated with infection (anthrax, for example). One of the PNAs is covalently attached to a surface of a substrate while the other is free in solution and also bears a reporter molecule (biotin, for example). A sandwich-complex forms on the substrate surface only if the complementary DNA is present. Once the two PNAs are present next to one another, cross-reactive functional groups form a covalent bond so that the both PNAs are now attached to the surface. Once the both PNAs are attached to the surface, the surface may be washed extensively to remove impurities before a signal from the reporter molecule is developed.

Use of a DNA-promoted cross link to the surface is an advantageous aspect of this technology. In the non-covalent complexes (where the complex is held together only by hydrogen bonds), washing the surface is inherently tricky: too little washing and impurities interfere with the detection signal, too much washing and the complex is removed from the surface. In our cross-linked technology, excess washes will not remove the second PNA from the surface and this helps to improve the quality of signal over the non-covalent versions of nucleic acid detection.

The benefits of using Peptide Nucleic Acids (PNAs) include: (i) neutral backbone leads to increased duplex stability over DNA, (ii) enzyme degradation minimized by non-natural backbone, (iii) synthesis from well established and efficient SPPS procedures (Boc- or Fmoc-) is available, and (iv) greater sequence selectivity over DNA. Numerous PNA variations are know in the art. These include compositions represented by the following structures.

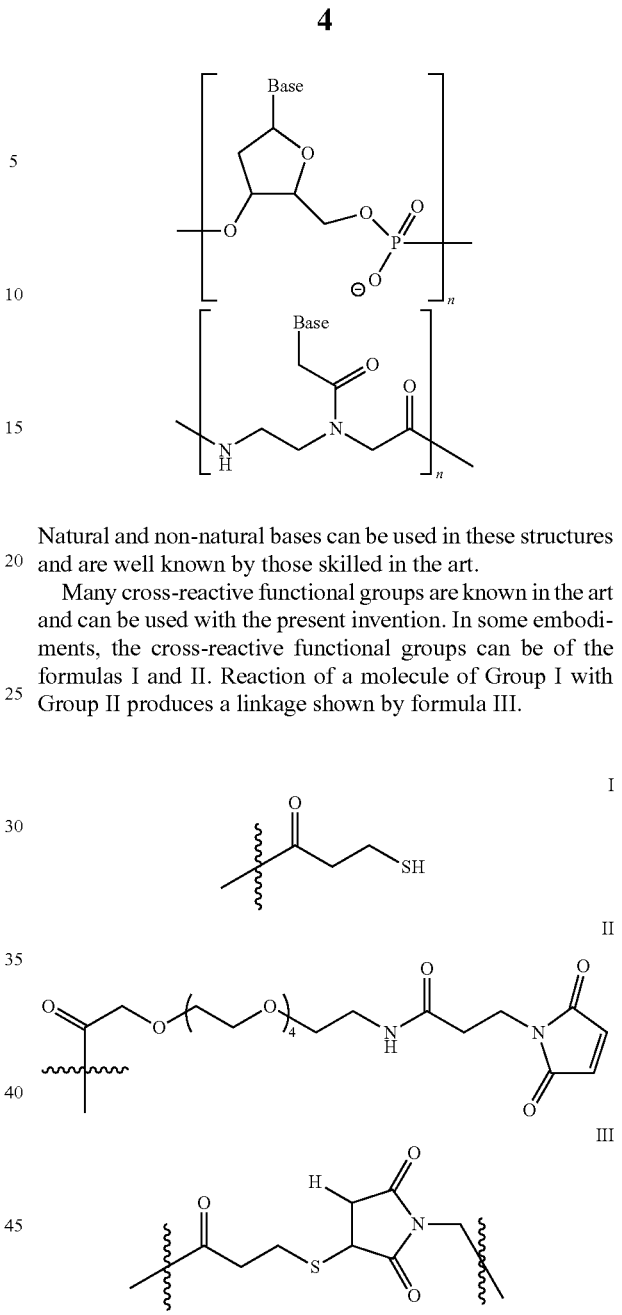

Natural and non-natural bases can be used in these structures and are well known by those skilled in the art.

Many cross-reactive functional groups are known in the art and can be used with the present invention. In some embodiments, the cross-reactive functional groups can be of the formulas I and II. Reaction of a molecule of Group I with Group II produces a linkage shown by formula III.

In some constructs, Groups I and II can be placed in a terminal position of the PNA chain. One of these groups can be placed on the PNA that is attached to a surface and the other group can be placed on the PNA that is free in solution. Typically, a reporter group is attached to the PNA that is free in solution.

As used herein, the term "reporter molecule" is to be understood to mean any group which is detectable by analytical means in vitro and/or in vivo and which confers this property to his property to the conjugate. Some reporter molecules are a fluorescent molecule having fluorescence properties which are a function of the concentration of the molecule. Other reporter molecules have a absorbance spectra that can be monitored for detection. Numerous reporter molecules are known to those skilled in the art and are suitable for use with the present invention. One preferred reporter molecule is biotin.

The term "cross reactive groups" refers to at least two groups that are capable of reacting to form a covalent bond linking the first and second PNAs.

Cross-linking reactive groups can be incorporated into PNAs by known techniques. In some embodiments, the cross-linking functional groups are attached in a terminal position in the PNA.

HRP Streptavidin consists of streptavidin protein that is covalently conjugated to horseradish peroxidase (HRP) enzyme. Streptavidin binds to biotin and the conjugated HRP provides a high level of activity for detection using an appropriate substrate system. In some preferred embodiments, the HRP can be a polymerized form of HRP. The commercially available complex is known to specifically react with biotin.

Some preferred PNAs contain trans-1,2-diaminocyclopentane which can potentially impact a broad range of scientific disciplines. Recent advances have improved the synthesis of trans-1,2-diaminocyclopentane. See, PCT Patent Application No. PCT/US2007/020466. These methods allow each nitrogen atom of cyclopentanediamine to be easily derivatized with identical or dissimilar groups.

Incorporation of trans-1,2-diaminocyclopentane into Peptide Nucleic Acids (PNAs) has a beneficial effect on the recognition of DNA and RNA sequences. As shown herein, this compound can be used in the development of nucleic acid detection kits for various pathogens.

Trans-1,2-diaminocyclopentanes can be prepared by ring-opening of an appropriate aziridine with an azide nucleophile in the presence of a promoter. In this way, two amine groups or its equivalents are installed in one step, thus circumventing the tedious functional group transformations. One such compound is trans-tert-butyl-2-aminocyclopentylcarbamate (1).

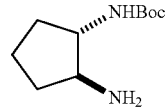

rac-1

A scheme for producing rac-1 is illustrated by Scheme I.

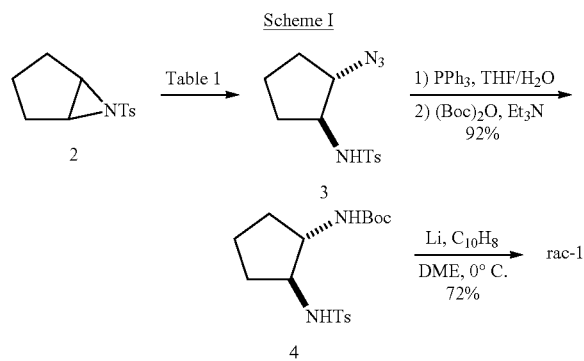

In one embodiment, the synthesis begins with ring opening of tosyl-activated aziridine 2 (Scheme 1, Table 1), which is readily accessible in one step from commercially available cyclopentene.

Without further purification, 3 can be reduced to the corresponding amine by Pd-catalyzed hydrogenation or Staudinger reduction (PPh$_3$, THF/H$_2$O). Those skilled in the art appreciate that other reactions may be used to convert 3 to the corresponding amine. Subsequent Boc protection of the resulting amine yielded 4 in 92% yield for two steps. Each of the aforementioned reactions are well known to those skilled in the art.

While this method is illustrated with the Boc protecting group, it is understood by those skilled in the art that other suitable protecting groups can be substituted. Additional protecting groups include any carbamate-based nitrogen protecting group. Examples of suitable protecting groups include fluorenyl-methoxy-carbonyl (Fmoc), carbobenzyloxy (Cbz), and allyloxycarbonyl (Alloc).

Generally, the major drawback of tosyl-activated aziridine chemistry is that harsh conditions are required for the cleavage of the sulfonamide bond at a later stage of the synthesis. Recently, milder conditions have been developed in this context, and magnesium in methanol under ultrasonic conditions has been successfully applied to a variety of substrates. Under these conditions, 4 underwent clean but very sluggish conversion. After considerable experimentation, the detosylation was achieved with lithium and naphthalene in dimethoxyethane (DME) or tetrahydrorfuran (THF). The reaction was temperature-dependent: at low (−78° C.) or room temperature, either very slow conversion (10%) was observed or low yield (40%) resulted. In one embodiment, the reaction was best performed at 0° C. for 5 h to afford 1 in 72% yield.

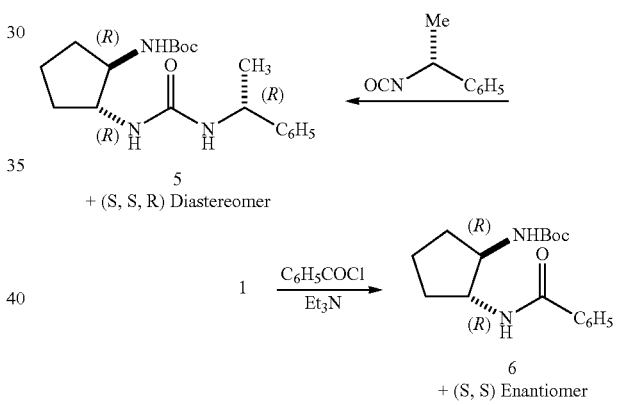

The resolution of primary amines with similar structures to 1 has been typically performed with tartaric acid or mandelic acid. Our initial attempts to resolve 1 with these two acids did not give precipitate under various conditions. Therefore, twenty other chiral resolving acids were screened. The resolution results were rapidly examined by $^1$H NMR method as follows (Scheme II): the precipitated salts were converted to amine 1 and subsequently treated with optically pure R-(+)-1-phenylethylisocyanate in CDCl$_3$, to give corresponding urea disastereomers 5. The Boc groups of the two diastereomers 5 showed separated peaks at 1.30 and 1.44 ppm in the $^1$H NMR. Among the different chiral acids that were screened, di-p-toluoyl-tartaric acid, 2-phenylpropionic acid, and menthyloxyacetic acid showed partial resolution. Fortunately, optimal results were obtained when 10-camphorsulfonic acid (CSA) was used as a resolving agent. The precipitate from rac-1 and CSA (1:1 or 1:0.5) in acetone showed approximately 60% ee.

After crystallizations from acetonitrile, the optical purity of 1 was enhanced to over 99% enantiomeric excess (ee), as determined by HPLC analysis (on a chiral stationary phase) of the benzoylated derivative 6. The configuration of 1 obtained from the resolution was assigned based on the comparison of HPLC data of 6 (obtained on a chiral stationary phase) to material obtained from previous syntheses performed in our laboratory.

Among the end uses of compound 1 is incorporation into the backbones of PNAs. The PNAs of the instant invention can be used in methods for detecting a nucleic acid comprising contacting a sample suspected of containing the nucleic acid with a peptide nucleic acid prepared in accordance with the invention. These PNAs can be used in a kit for detecting a nucleic acid comprising at least one peptide nucleic acid prepared in accordance with the invention. The kits can be adapted for detecting an infectious agent, the infectious agent such as anthrax, avian flu, tuberculosis, severe acute respiratory syndrome (SARS), human papilloma virus (HPV), or human immunodeficiency virus (HIV). This list of agents is illustrative only and those skilled in the art are aware of other infectious agents that can be detected with the use of PNAs comprising 1,2-diaminopentane residues in the PNA backbone.

Chemical modification in the backbone of a peptide nucleic acid (PNA) lowers the detection limit of anthrax DNA by six orders of magnitude compared to the regular, unmodified PNA. Furthermore, the modified-PNA has improved sequence specificity compared to regular PNA, and is a key component of a colorimetric detection system for anthrax DNA. These findings make PNA a highly desirable probe for incorporation into DNA detection devices, and should stimulate the replacement of traditional DNA probes.

Figure 2:
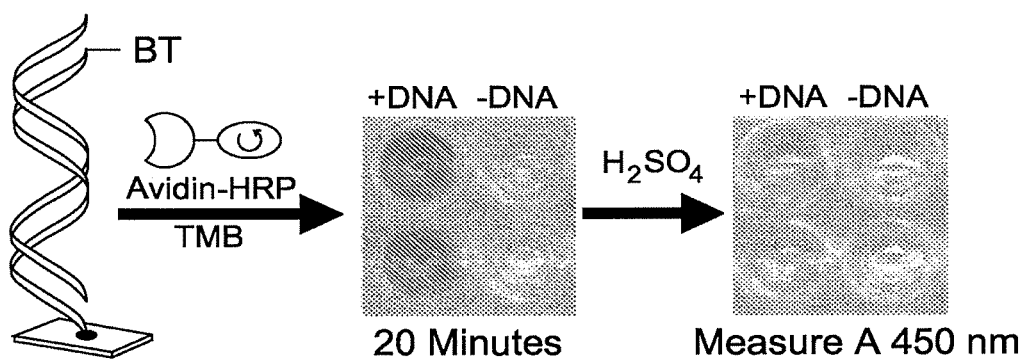
FIG. 2 illustrates signal amplification from PNA-based sandwich-hybridization using PNAα(2) and PNAβ(2) with 103 fmol DNA and HRP-avidin. Four wells of a 96-well plate are shown, and each column represents identical conditions. Blue color results from initial oxidation of 1-Step TurboTMB, and yellow color is produced once the enzymatic reaction is stopped.
Figure 3:
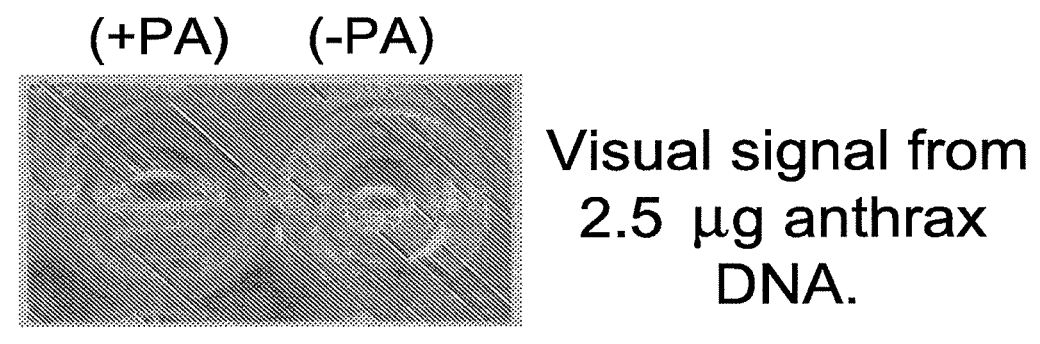
Figure 4:
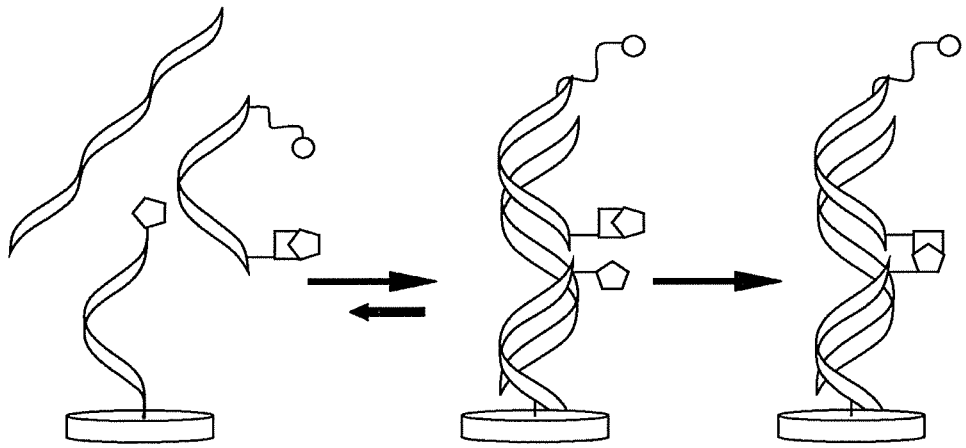
FIG. 4 illustrates the covalent cross-linking approach. A solution comprising a first PNA containing a first cross-reactive functional group and a reporter molecule and a substrate to which a second PNA containing a second cross-reactive functional group is attached, is contacted with a sample suspected of containing a nucleic acid. Once the two PNAs are present next to one another, cross-reactive functional groups form a covalent bond so that the both PNAs are now attached to the surface.
Figure 4:
Figure 4:
Figure 4:
Figure 5:
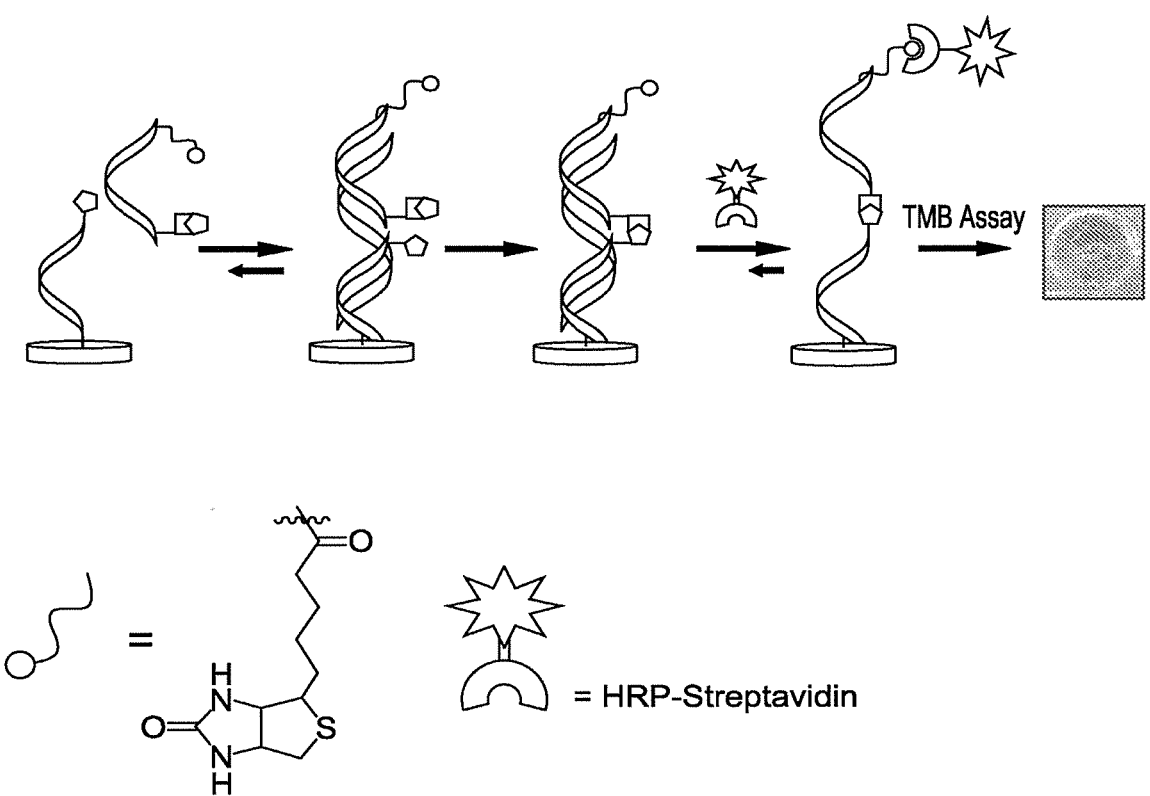
FIG. 5 illustrates use of horseradish peroxidase (HRP)-streptavidin to increase detection limits. Detection Limits were determined to be 10 fmol ($10 \cdot 10^{-15}$ mol) DNA with regular aegPNA and 10 zmol ($10 \cdot 10^{-21}$ mol) DNA with tcyp-PNA.

Technologies for genomic detection most commonly use DNA probes to hybridize to target sequences. To achieve required sensitivity, the use of PCR to amplify target sequences has remained standard practice in many labs. Direct detection methods that eliminate the requirement for a PCR step could afford faster and simpler devices that can be used outside of a laboratory. Devices based on nanotechnology have yielded impressive results, yet the use of PCR is still predominant in most applications. However, replacing DNA probes with a class of synthetic nucleic acids, such as peptide nucleic acids (PNAs), can significantly improve detection devices. There are numerous advantages to using PNA instead of DNA probes in hybridization assays, including: complete resistance to degradation by enzymes, increased sequence specificity to complementary DNA, and higher stability when bound with complementary DNA. Despite these advantages, the use of PNA in DNA detection systems has received sparse attention, and has not replaced the use of DNA probes. We believe that one reason PNA does not dominate in this area is due to the lack of backbone modifications that can be used to adjust the properties of a probe sequence. Without the ability to improve and fine-tune the basic properties of PNA, it is likely not worth the effort and/or funds for researchers to switch from DNA to PNA probes. We have developed a system of chemical modifications for PNAs, using cyclopentane groups, to predictably improve the melting temperature and sequence specificity of PNA-DNA duplexes. To demonstrate the utility of our chemical strategy and to highlight the importance of PNA in detection, we developed a simple, colorimetric sandwich-hybridization assay to detect anthrax lethal factor DNA using PNA as capture and detection probes (FIGS. 1 and 2). Our system has been developed into a convenient 96-well plate format in which the capture probe (PNAα) is covalently attached to a DNA-Bind® plate. A biotin-labeled PNA detection probe (PNAβ), in combination with commercially available avidin-horseradish peroxidase conjugate (avidin-HRP) and tetramethylbenzidine (TMB), is used to generate a signal if the target DNA is present. If a sandwich complex forms on the plate, the strong interaction between biotin and avidin will retain avidin-HRP on the plate. The HRP will then catalyze oxidation of TMB, and after stopping the reaction with sulfuric acid a colored product that absorbs at 450 nm is generated. These items are accessible to most biomedical research facilities. Incorporation of a cyclopentane-modified PNA residue (tcyp) into the capture probe (PNAα(1)) affords a system with a detection limit of 50 zeptomoles for lethal factor DNA, which is 6 orders of magnitude lower compared to the same system that uses regular, unmodified PNA (PNAα (2)) (FIG. 3 and Table 5). Furthermore, the sequence specificity is improved in the tcyp-modified PNA compared to the regular PNA.

Finally, we have demonstrated that our detection system effectively identifies lethal factor DNA from a whole cell extract of *B. anthracis* DNA, giving a colored signal visible to the naked eye (FIG. 2). The stability of PNAs, and the ability to synthesize PNAs of different sequences should allow the development of effective detection systems for numerous bacterial and viral pathogens (such as HIV and Avian flu), as well as single nucleotide polymorphisms associated with several diseases (such as cancer and Alzheimer's disease). Furthermore, the ability to introduce chemical modifications with predictable effects into the PNA should allow researchers to fine-tune the properties of PNA for a specific application, and this flexibility could provide robust genomic detection devices available to healthcare workers in the field and to the general public.

Experimental Section

2-Azido-N-tosyleyclopentanamine (3)

To a mixture of 6-tosyl-6-aza-bicyclo[3,1,0]hexane 2 (20.0 g, 84.4 mmol) and $NaN_3$ (5.5 g, 84.4 mmol) in dry THF (300 mL) was added TMSN, (2.9 g, 3.0 mL, 25.3 mmol), followed by the addition of TBAF (25.3 mL, 1M in THF, 25.3 mmol). The solution was stirred at 40° C. for 20 h. The reaction solution was cooled to room temperature, saturated $NaHCO_3$ aqueous solution (200 mL) was added. The aqueous layer was extracted with diethyl ether (100 mL×3). Combined organic layers were washed with brine (100 mL), dried over $Na_2SO_4$, filtered, and concentrated under vacuum. The oil residue was filtered through a pad of silica gel and washed with a mixture of ethyl acetate/hexanes (1:2, 2000 mL). Solvents were removed under vacuum to afford 3 (22.4 g, 95%) as a colorless oil. Spectroscopic data of 3 were consistent with the literature data for this compound.

The reaction to produce 3 was repeated with a variety of conditions. These are summarized in the table below.

TABLE 1

Ring Opening Of Aziridine 2 with Azides.

| Entry | Reagents | Solvent | Temp (° C.) | Time (h) | Conversion (%)[b] | Yield (%)[c] |
|---|---|---|---|---|---|---|
| 1 | $NaN_3$, ozone | $CH_3CN/H_2O$ | 23 | 5 | 0 | 0 |
| 2 | $NaN_3$, 10% CAN | $CH_3CN/H_2O$ | 23 | 20 | 15 | 13 |
| 3 | $TMSN_3$ | DMF | 40 | 16 | 34 | 30 |
| 4 | $TMSN_3$, 5% TBAF | THF | 40 | 16 | 81 | 76 |
| 5 | $TMSN_3$, 20% TBAF | THF | 40 | 16 | 100 | 93 |
| 6 | $TMSN_3$, 00% TBAF | THF | 40 | 4 | 100 | 96 |

TABLE 1-continued

Ring Opening Of Aziridine 2 with Azides.

| Entry | Reagents | Solvent | Temp (° C.) | Time (h) | Conversion (%)[b] | Yield (%)[c] |
|---|---|---|---|---|---|---|
| 7 | 30% TMSN$_3$, 30% TBAF, 100% NaN$_3$ | THF | 40 | 20 | 100 | 95 |

[a]All reactions were conducted at 4 mmol scale entries 5-7 were also conducted at ~85 mmol scale.
[b]Determined by $^1$H NMR.
[c]Isolated yield.

A literature search revealed four examples of ring-opening of 2 with azides. However, our examination of these methods revealed that none of them gave satisfactory results, especially for large-scale (4 mmol scale) synthesis. For instance, attempted opening of 2 with NaN$_3$ using Oxone in aqueous acetonitrile failed to provide any ring-opening products. The use of ceric ammonium nitrate (CAN) instead of Oxone led to 15% conversion and 13% yield of 3. Similar results were observed when TMSN$_3$ in DMF was used. Fortunately, adding 5% TBAF to TMSN$_3$ significantly promoted the transformation (entry 4, 80% conversion, 76% yield). However, the operation requires laborious column chromatography to separate azido amine product 3 from unreacted 2, which has an Rf value close to that of 3. Complete conversion was achieved by increasing the amount of TBAF to 20% (entry 5). If 1 equivalent TBAF is used, the reaction time can be shortened to 4 h and 3 can be obtained in 96% yield (entry 6). Similar results can be obtained, although with longer reaction times, by using 30% TMSN$_3$, 30% TBAF, and 100% NaN$_3$ (entry 7). In some embodiments, these final conditions prove to be the most cost-effective and reliable for preparation of 3.

tert-Butyl-2-(tosylamino)cyclopentylcarbamate (4)

Triphenylphosphine (40.3 g, 153.8 mmol) was added to a solution of 3 (21.5 g, 76.9 mmol) in THF/H$_2$O (600/50 mL). The mixture was stirred at room temperature for 16 h. 1M HCl solution (200 mL) was added. The aqueous layer was separated, extracted with diethyl ether (200 mL×3), and basified with 2 N NaOH solution to pH 12-14. The aqueous solution was extracted with ethyl acetate (200 mL×5). Combined organic layers were washed with brine (100 mL), dried over Na$_2$SO$_4$, filtered, and concentrated under vacuum to afford a light yellow oil (18.9 g, 97%). Without further purification the resulting oil was dissolved in dry methylene chloride (360 mL), di-tert-hutyldicarhonate (15.6 g, 71.6 mmol) and triethylamine (10 mL) were added. The solution was stirred at room temperature for 16 h. Most of the solvent was removed under vacuum, and diethyl ether (300 ml,) was added. The mixture was with 1 N HCl solution (50 mL×3), dried over Na$_2$SO$_4$, and concentrated to afford a white solid which crystallized from diethyl ether to give white needles (24.9 g, 92% for two steps). Rf=0.36 (hexanes/EtOAc 2:1). Mp: 129-130° C. IR (film) 3680, 2973, 2844, 2866, 1685, 1346, 1160, 1055, 1012 cm$^{-1}$. $^1$H NMR (300 MHz: CDCl$_3$) δ 7.75 (d, ZH), 7.26 (d, 2H), 6.19 (s, br, 1H), 4.55 (s, hr, 1H), 3.70 (m, 1H), 3.03 (m, 1H), 2.42 (s, 3H), 2.02 (m, 2H), 1.65 (m, 3H), 1.42 (s, 9H), 1.30 (m, 1H). $^{13}$C NMR (75 MHz, CDCl$_3$) δ 156.9, 143.1, 137.4, 129.6, 127.2, 80.1, 61.7, 57.1, 31.3, 29.4, 28.4, 21.6, 20.2. HRMS (EI) m/z calcd for C$_{17}$H$_{27}$N$_2$O$_4$S [M+1]$^+$ 353.1535, found 353.1554.

tert-Butyl-2-aminocyclopentylcarbamate (1)

A mixture of lithium granules (1.52 g, 226.6 mmol) and naphthalene (10.9 g, 85.0 mmol) in dry dimethoxyethane (350 mL) were stirred at room temperature for 2 h. The deep blue solution was then cooled to 0° C., a solution of 4 (10.0 g, 28.33 mmol) in dry dimethoxyethane (40 mL) was added dropwise over 20 min. The mixture was stirred at 0° C. for 5 h. The undissolved lithium was filtered off, and 1 N HCl solution (60 mL) was added to the filtrate. The organic layer was separated and extracted with 1 N HCl (50 mL×2). The aqueous layers were combined, extracted with diethyl ether (50 mL×3), and then basified with 2 N NaOH solution to pH 12-14. The aqueous solution was extracted with ethyl acetate (50 mL×5). Organic layers were combined, dried over Na$_2$SO$_4$, solvent was removed under vacuum to afford rac-1 as a colorless oil, which solidified under vacuum to a white solid (4.08 g, 72%). Rf=0.31 (hexanes/EtOAc 2:1). Mp 60-62° C. IR (film) 3301, 2967, 1689, 1526, 1453, 1390, 1365, 1250, 1170, 1045, 1020, 870, 781 cm$^{-1}$. $^1$H NMR (300 MHz, CDCl$_3$) δ 4.48 (s, hr, 1H), 3.48 (m, 1H), 2.99 (m, 1H), 2.14 (m, 1H), 1.98 (m, 1H), 1.70 (m, 2H), 1.45 (s, 9H), 1.38 (m, 2H). $^{13}$C NMR (75 MHz, CDCl$_3$) δ 156.1, 78.9, 60.5, 59.4, 33.0, 30.9, 28.4, 20.7. HRMS (EI) m/z calcd for C$_{10}$H$_{21}$N$_2$O$_2$ [M+1]$^+$ 201.1603, found 201.1632.

Optical Resolution of tert-Butyl-2-aminocyclopen+arbamate (1) using (S)-(+)-10-Camphorsulfonic acid (S)-(7)-10-Camphorsulfonic acid (8.24 g, 35.5 mmol) in acetone (HPLC grade, 20 mL) was added to a solution of rac-1 (7.1 g, 35.5 mmol) in acetone (HPLC grade, 20 mL). The mixture was stirred for 6 h and the resulting white precipitate was collected by filtration. The precipitate was recrystallized in acetonitrile twice. The white precipitate was taken up in a mixture of ethyl acetate and 2 N NaOH solution. The aqueous layer was extracted with ethyl acetate (30 mL×3). The organic layers were combined, dried over Na$_2$SO$_4$. The solvent was removed under vacuum to give a colorless oil (2.34 g, 11.7 mmol), which was dissolved in acetone and treated with a solution of (S)-(+)-10-camphorsulfonic acid (2.71 g, 11.7 mmol) in acetone (HPLC grade, 20 mL). After stirring for 2 h, solvent was evaporated and solid was crystallized from acetonitrile. The same workup procedure described above to make the free base gave a colorless oil which solidified under vacuum to give a white solid (S,S-1: 1.90 g, 51% based on one enantiomer). [α]$^{23}_D$+15.8 (c 1.0, EtOH); Mother liquid was basified and extracted with ethyl acetate, resolved with (R)-(−)-10-camphorsulfonic acid following the procedure described above to afford R,R-1 (1.58 g, 46% based on one enantiomer): [α]$^{23}_D$-16.0 (c 1.0, EtOH).

Resolution Experiments with Other Chiral Acids.

Rac-1 was contacted with various chiral acids as shown in Table 2. Conditions were as described for (S)-(+)-10-camphorsulfonic acid. Preferably, conditions where the combination of the compound and a chiral acid dissolves with some heat, and then precipitates when cooled. Ideally, only one enantiomer would precipitate out of solution with the chiral acid. In Table 2, a few conditions (including use of ethanol, acetone with some methanol, and isopropanol) are reported. The enantiomeric ratio (er) indicates whether the chiral acid showed potential as a resolving agent. For a number of the chiral acids tested, under most conditions, the salt did not dissolve well, or dissolved too well and never precipitated (NP). In some cases a precipitate forms but the er is 1:1, which showed non-specific precipitation. The best result was with entry number 5 of Table 2. We believe, however, that there are many other chiral acids and many other conditions which can produce favorable results.

Scheme III

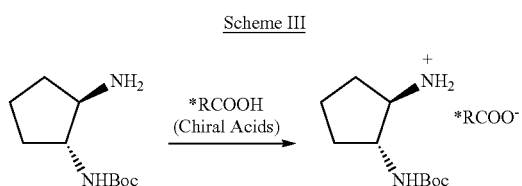

TABLE 2

Use of Chiral Acids as Resolving Agents

| | Chiral Acid | Ethanol | Acetone (+MeOH) | Isoporpanol |
|---|---|---|---|---|
| 1 | Dibenzoyl-L-tartaric acid monohydrate | Waxes | Dissolved, NP | |
| 2 | (−)-O,O'-Di-p-toluyl-L-tartaric acid | Waxes | Not dissolved well, er: 2:1 | Not completely dissolved |
| 3 | (1S)-(−)-Camphanic acid | Waxes | Not dissolved well, er: 1:1 | |
| 4 | (1R,3S)-(+)-Camphoric acid | Insoluble | Not dissolved well, er: 1:1 | |
| 5 | (1R)-(−)-10-Camphorsulfonic acid | Waxes | Dissolved (heated), er: 4:1 | |
| 6 | (R)-(−)-4-Bromomandelic acid | Waxes | Dissolved, NP | |
| 7 | (R)-(−)-4-Methylmandelic acid | Waxes | Dissolved, NP | |
| 8 | (R)-(−)-3-Chloromandelic acid | Waxes | Dissolved, NP | |
| 9 | (R)-(−)O-Acetylmandelic acid | Waxes | Dissolved, NP | |
| 10 | (R)-(−)-2-Chloromandelic acid | Waxes | Dissolved, NP | |
| 11 | L-Malic acid | Waxes | Dissolved, NP | |
| 12 | (S)-(+)-2-Phenylpropionic acid | Waxes | Dissolved (heated), er: 3:1 | |
| 13 | (S)-(+)-α-Methoxyphenylacetic acid | Waxes | Dissolved (heated), er: 1:1 | |
| 14 | L-Menthoxyacetic acid | Waxes | Dissolved, er: 5:4 | |
| 15 | (R)-(+)-Tetrahydro-2-furoic acid | Waxes | Dissolved, NP | |
| 16 | (R)-(−)-2,2'-(1,1'-Binaphthyl)phosphoric acid | Waxes | Dissolved, NP | |
| 17 | (−)-O,O'-Dibenzoyl-L-tartaric acid mono(dimethylamide) | Waxes | Dissolved, NP | |
| 18 | (−)-2'-Bromotartranilic acid | Waxes | Dissolved, NP | |
| 19 | (+)-2'-Methyltartranilic acid | Waxes | Dissolved, NP | |
| 20 | (+)-2'-Nitrotartarnilic acid | Waxes | Dissolved (heated), NP | |

NP: No Precipitate, er: enantiomeric ratio

HPLC Analysis of
tert-Butyl-2-(benzamido)cyclopentylcarbamate (6)

Benzoyl chloride (20 mg, 0.016 mL, 0.14 mmol) was added to a solution of nonracemic 1 (28 mg, 0.14 mmol) and triethylamine (28 mg, 0.038 mL, 0.28 mmol) in dry methylene chloride (2 mL). The solution was stirred for 16 h, and then washed with 1 M HCl solution (1 mL×3). Organic layer was dried over $Na_2SO_4$, solvent was removed under vacuum, and the residue was purified by preparative TLC (solvent: hexanes/EtOAc 2:1) to afford 5 (38 mg, 85%) as a white solid. Rf=0.29 (hexanes/EtOAc 2:1). Mp 190-192° C. IR (film) 3314, 2974, 1638, 1621, 1541, 1302, 1170, 1033 $cm^{-1}$. $^1H$ NMR (300 MHz, $CDCl_3$) δ 7.75 (m, 2H), 7.34 (m, 3H), 4.75 (s, br, 1H), 3.85 (s, br, 2H), 2.33 (m, 1H), 2.04 (m, 1H), 1.72 (m, 2H), 1.39 (m, 2H), 1.34 (s, 9H). $^{13}C$ NMR (75 MHz, $CDCl_3$) δ 168.0, 157.1, 134.3, 131.4, 128.5, 127.1, 80.0, 59.2, 56.5, 30.1, 29.8, 28.8, 28.4, 19.6. HRMS (EI) m/z calcd for $C_{10}H_{21}N_2O_2$ $[M+1]^+$ 327.1685, found 327.1689.

Compound 6 was dissolved in 2-propanol/hexanes (1:1) for HPLC analysis. HPLC conditions: column. (S,S)-Whelk-O1, 250 mm×4.6 mm, 10 micron supplied by Regis Technologies; mobile phase: hexanes/2-propanol (95:5); flow rate: 1.5 mL/min; absorbance 0.04; sample concentration: 1 mg/mL; injection volume: 20 μL; retention time: S,S-1, 7.07 min; R,R-1, 9.53 min.

$^1H$ and $^{13}C$ NMR data was obtained for compounds 1, 4, and 6. HPLC data was obtained on a chiral stationary phase for compound 6.

PNA Synthesis and Detection of Infectious Agents.

Methods for PNA and cyclopentane-modified PNA synthesis and acquisition of melting temperature data can be found in Pokorski, et al., J. Am. Chem. Soc. 2004, 126, 15067. Addition of one or more cyclopentane groups into a PNA sequence improves the melting temperature to complementary DNA by ~5° C. per cyclopentane, regardless of which base is used.

To demonstrate the utility of our chemical strategy and to highlight the importance of PNA in detection, we report a simple, colorimetric sandwich-hybridization assay to detect anthrax protective antigen DNA using PNA. In this system, a key component to improving the detection limit and sequence specificity is the incorporation of a cyclopentane-modified PNA into the surface-bound probe. In the sandwich-hybridization strategy, one PNA is used as capture probe (PNAα) to recruit complementary DNA to a surface, and another PNA is used as a detection probe (PNAβ) to generate a signal (FIG. 1). This assay has been developed into a convenient 96-well plate format in which PNAα is covalently attached to a DNA-Bind plate. A biotin-labeled PNAβ, in combination with commercially available avidin-horseradish peroxidase conjugate (HRP-avidin) and tetramethylbenzidine (TMB), is used to generate a signal if the target DNA is present. If a sandwich complex forms on the surface, the strong interaction between biotin and avidin will retain HRP-avidin. The HRP will then catalyze oxidation of TMB, and after stopping the reaction with sulfuric acid, a colored product that absorbs at 450 nm is generated. These items are accessible to most biomedical research facilities.

In the construction of PNA probes, all PNAs were made with a single sequence that corresponds to the protective antigen (PA) portion of the anthrax genome, which is highly conserved. See, Edwards, K. A.; Clancy, H. A.; Baeumner, A. J. Anal. Bioanal. Chem. 2006, 384, 73-84. Next, PNAR probes were designed with extended linkers on the N-terminal for covalent attachment to the DNA-Bind plate. The PNAβ probes were outfitted with additional lysine groups so that biotins could be attached. To ensure that there was enough room for the HRP-avidin complex to bind, additional linkers were added onto the lysine side chains (Table 3).

TABLE 3

PNA Capture Probes (α) and PNA Detection Probes (β)

| entry | PNA sequence[a] | $T_m$ (° C.)[b] |
|---|---|---|
| α(1) | H$_2$N-(egl)$_5$-ATCCTTATCAATATT-CONH$_2$ | 50.5 |
| α(2) | H$_2$N-(egl)$_5$-ATCCTTAT$_{tcyp}$CAATATT-CONH$_2$ | 55.6 |
| β(1) | H$_2$N-TAACAATAATCC-Lys-Lys-CONH$_2$<br>                                     (egl)$_2$BT | 54.1 |
| β(2) | H$_2$N-TAACAATAATCC-Lys-Lys-Lys-CONH$_2$<br>                           Bt(egl)$_2$(egl)$_{10}$BT | 55.1 |

[a]tcyp = PNA residue derived from (S,S)-trans-1,2-cyclopentane diamine, BT = biotin, egl = 8-amino-3,6-dioxaoctanoic acid.
[b]Tm represents the melting temperature for the duplex formed between the indicated PNA and antiparallel DNA. Conditions for Tm measurement: 150 mM NaCl, 10 mM sodium phosphate buffer, pH 7.0, 0.1 mM EDTA, UV measured at 260 nm from 90 to 25° C., in 1° C. increments.
All values are averages from two or more experiments.
α(1) = SEQ ID NO. 5;
α(2) = SEQ ID NO. 6;
β(1) = SEQ ID NO. 7;
β(2) = SEQ ID NO. 8;

PNAα probes were attached to the surface of each well of the DNA-Bind plate, and free sites were blocked using a buffer consisting of BSA and lysine. Detection conditions were optimized using synthetic DNA. Ultimately, a set of conditions were developed that involve incubating a solution of target DNA and PNAβ in the well of a DNA-Bind plate that contains PNAα, followed by washing, incubation with HRP-avidin, another washing, and then detection with 1-Step Turbo TMB, a commercially available TMB and peroxide solution. The enzymatic reaction was stopped by the addition of sulfuric acid, and then absorbance at 450 nm was measured. Using unmodified PNA under these conditions, only picomole quantities of DNA could be detected (Table 4, entry 4).

TABLE 4

Absorbance at 450 nm for DNA Detection with Different PNA Probes and Using HRP-Avidin (entries 1-4) versus Poly-HRP-avidin (entries 5-8)

| | | Femtomoles of Anthrax DNA | | | |
|---|---|---|---|---|---|
| entry | PNAs[a] | $10^3$ | $10^1$ | $10^{-1}$ | $10^{-6}$ |
| 1 | α(2) + β(2) | 0.23 | 0.02 | 0.01 | 0.01[b] |
| 2 | α(2) + β(1) | 0.16 | 0.01 | — | — |
| 3 | α(1) + β(2) | 0.19 | 0.01 | — | — |
| 4 | α(1) + β(1) | 0.12 | — | — | — |
| 5 | α(2) + β(2) | 0.99 | 0.15 | 0.15 | 0.09[c] |
| 6 | α(2) + β(1) | 1.05 | 0.03 | 0.01 | 0.01[c] |
| 7 | α(1) + β(2) | 0.44 | 0.01 | — | — |
| 8 | α(1) + β(1) | 0.20 | — | — | — |

[a]See Table 3 for structures of PNAs. Standard deviation values for absorbances range from 0.01 to 0.03. All experiments in Table 4 were performed with synthetic anthrax DNA sequences.
[b]Data for 50 zmol DNA.
[c]Data for 10 zmol DNA.

Several strategies were explored to boost the detection signal and lower the DNA detection limit. A tcyp-modified PNA residue was incorporated into PNAα (PNAα(2)), an additional biotin was attached to PNAβ (PNAβ(2)), and a commercially available polymer of HRP-avidin (poly-HRP-avidin) was used in which the ratio of HRP to avidin is approximately 40:1. Table 4 represents the absorbance values at 450 nm (over background) obtained when using different combinations of PNAα and PNAβ at several different concentrations of synthetic DNA and when using HRP-avidin (entries 1-4) and poly-HRP-avidin (entries 5-8). The results of Table 4 demonstrate that all these strategies help improve the signal associated with DNA detection and lower the overall DNA detection limit. In the best combination (entry 5), 10 zmol of DNA can be detected.

Compared to unmodified PNA, incorporation of tcyp into PNA can improve the discrimination of single base mismatches in DNA. See, Pokorski, et al., *J. Am. Chem. Soc.* 2004, 126, 15067-15073. In the context of the detection assay, we examined the changes in absorbance at 450 nm associated with single base mismatches for tcyp PNA versus regular PNA. The results in Table 5 show that, under the same conditions, the tcyp PNA (PNAα(2)) shows much clearer differences in signal between matched and mismatched DNA sequences than the regular PNA (PNAα(1)).

TABLE 5

Absorbance at 450 nm for Detection of Mismatches Located Directly Across from the tcyp in PNAR(2) and Comparison with Unmodified PNAα(1)[a]

| | Mismatch Comparison at $10^3$ fmol Anthrax DNA | | | |
|---|---|---|---|---|
| PNAs[a] | none | TG | TC | TT |
| α(2) + β(2) | 0.31 | 0.05 | 0.04 | 0.05 |
| α(1) + β(2) | 0.12 | 0.04 | 0.01 | 0.04 |

[a]See above for DNA sequences used in detection. Standard deviation values for absorbances range from 0.01 to 0.05. All experiments in Table 5 were performed with synthetic anthrax.

Using the most sensitive detection system from our research, we examined the ability to detect protective antigen (PA) DNA obtained from a whole cell extract of *B. anthracis*. In this study, DNA was extracted from two cell lines of anthrax, one that has PA-DNA (Ames 35) (see, Green, et al., *Infect. Immun.* 1985, 49, 291-297. and one that lacks PA-DNA (Ames 33) (see, Pomerantsev, et al., *Infect. Immun.* 2006, 74, 682-693). Our detection system was clearly able to distinguish the two cell lines, giving a colored signal visible to the naked eye (FIG. 3). The high thermal stability of PNA-DNA duplexes allows shorter PNA probes to be used compared to DNA. A DNA-based system with equivalent thermal stability of the capture and probe sequences would require DNAs ~30-45 bases long, which could reduce sequence specificity. The ability to introduce chemical modifications with predictable effects into the PNA allows us to equalize the Tm's of the two PNA probes for their DNA targets, which likely promotes uniform hybridization of all probes.

All PNA oligomers were purified by reverse-phase HPLC with UV detection at 260 nm using VYDEK C18 (d=10 mm, l=250 mm, 5 microns) semi-prep column, eluting with 0.05% TFA in water (Solution A) and 0.05% TFA in acetonitrile (Solution B). An elution gradient of 100% A to 100% B over ~30 minutes at flow rate of 5 mL/min. PNAs were characterized by electrospray mass spectroscopy. All PNA oligomers gave molecular ions consistent with the final product (Table 6).

TABLE 6

Mass Characterization Data for PNAs

| Entry[a] | PNA Sequence | Calculated MW | Observed MW |
|---|---|---|---|
| α(1) | H$_2$N-(egl)$_5$-ATCCTTATCAATATT-CONH$_2$ | 4736.6 | 4736.8 |
| α(2) | H$_2$N-(egl)$_5$-ATCCTTAT$_{tcyp}$CAATATT-CONH$_2$ | 4776.7 | 4776.5 |
| β(1) | H$_2$N-TAACAATAATCC-Lys-Lys-CONH$_2$<br>                                   \|<br>                                   (egl)$_2$BT | 3994.1 | 3994.0 |
| β(2) | H$_2$N-TAACAATAATCC-Lys-Lys-Lys-CONH$_2$<br>                              \|   \|<br>                        Bt(egl)$_2$(egl)$_{10}$BT | 5800.1 | 5799.8 |

[a]The accurate mass Electrospary ionization (ESI) mass spectra were obtained on a Waters LCT Premier time-of-flight(TOF) mass spectrometer. The instrument was operated in W mode at a nominal resolution of 10000. The electrospary capillary voltage was 2 KV and the sample cone voltage was 60 volts. The desolvation temperature was 275 (° C.) and the desolvation gas was Nigrogen with a flow rate of 300 L/hr. Accurate masses were obtained using the internal reference standard method. The sample was introduced into the mass spectrometer via the direct loop injection method. Both positive and negative ion accurate mass data were achieved simply by reversing the instrument's operating polarity. Deconvolution of multiply charged ions was performed with MaxEnt I.
α (1) = SEQ ID NO. 5;
α (2) = SEQ ID NO. 6;
β (1) = SEQ ID NO. 7;
β (2) = SEQ ID NO. 8.

HRP-avidin, poly HRP-avidin, and 1-Step Turbo TMB were purchased from Pierce. DNA-BIND® 96-well plates were purchased from Corning Life Sciences. Absorbance values for the DNABIND® 96-well plates were determined on a Victor2 1420 microplate reader (Perkin Elmer Life Sciences).

The oligonucleotides listed in Table 7 were purchased from IDT and used in the research as indicated in Tables 4 and 5.

TABLE 7

DNA Sequences

| | |
|---|---|
| Anthrax PA: | 5'-GGA TTA TTG TTA AAT ATT GAT AAG GAT-3'; SEQ ID NO. 1 |
| TG mismatch: | 5'-GGA TTA TTG TTA AAT ATT GGT AAG GAT-3'; SEQ ID NO. 2 |
| TC mismatch: | 5'-GGA TTA TTG TTA AAT ATT GCT AAG GAT-3'; SEQ ID NO. 3 |
| TT mismatch: | 5'-GGA TTA TTG TTA AAT ATT GTT AAG GAT-3'; SEQ ID NO. 4 |

The following abbreviations are used herein: PBS (phosphate saline buffer: 137 mM NaCl, 10 mM sodium phosphate, 2.7 mM KCl, pH 7.0), 0.1×SSC (15 mM NaCl, 1.5 mM Sodium Citrate), SDS (Sodium Dodecyl Sulfate), TMB (3,3', 5,5'-tetramethylbenzidine), OBB (oligo binding buffer: 50 mM Na$_2$HPO$_4$/NaH$_2$PO$_4$, 1.0 mM EDTA), BB (blocking buffer: 3% BSA and 25 mM lysine in OBB, pH 7.0).

Attaching PNAα to Surface.

PNAα solution (1.0 μM) in OBB (110 μL, pH 7.5) was added to each well of a DNA-BIND® 96-well plate (Corning Life Sciences), incubated at 37° C. for 1 hr, then washed three times with PBS buffer.

DNA Detection Protocol.

Blank absorbance at 450 nm of the DNA-BIND® plate was obtained on the microplate reader. Each well was treated with 200 μL BB for 30 minutes at 37° C. Target DNA (10 nM to 5 aM) and PNAβ (15 nM) were premixed in 100 μL of 0.15 M aqueous NaCl, then loaded into each well. The plate was sealed with an adhesive film, incubated at 45° C. for 3 hours, then washed twice with 0.1% SDS in 0.1×SSC and treated with BB (200 μL) for 30 minutes at 33° C. Next, 100 μL of 1.0 μg/mL avidin-horseradish peroxidase conjugate in BB was added. After 30 minutes at 37° C., the plate was washed three times with PBS buffer. Next, 100 μL of 1-step turbo TMB was added and incubated at 37° C. for 20 minutes. Then, 2 M H$_2$SO$_4$ (50 μL) was added to stop the oxidation. The plate was scanned again at 450 nm to give experimental absorbance readings from which background readings were subtracted. In some cases, very similar absorbance readings were obtained for different concentrations (see Table 2, entry 5). Most of these situations arise when using the polymer of HRP-avidin (poly HRP-avidin). This polymeric construct is highly active and difficult to control at higher concentrations. It is certainly ideal for detection of low concentrations of DNA, but can become less active at higher concentrations. Therefore, we suspect that aggregation at higher concentrations could lower enzymatic activity and, in some cases, give similar absorbance readings for different DNA concentrations.

Bacterial Strains and Genomic DNA Purification.

*Bacillus anthracis* Ames 35 (pXO1$^+$ pXO2$^-$) strain. and a plasmid-free Ames 33 strain (pXO1$^-$ pXO2$^-$) were used for genomic DNA purification. Ames 35 harbors the pag gene that encodes PA, while Ames 33 does not ((see, Green, et al., *Infect. Immun.* 1985, 49, 291 and Pomerantsev, et al., *Infect. Immun.* 2006, 74, 682.). For genomic DNA purification, *B. anthracis* strains were grown at 37° C. in LB broth overnight. Genomic DNA purification was performed using the Wizard genomic DNA purification kit (Promega) following the protocol provided by the manufacturer and DNA was resuspended in water. DNA concentration was then assessed using a Nanodrop ND-1000 spectrophotometer (Coleman Technologies Inc).

PNAs Targeted to the DNA Region of a P-gp.

PNA has been previously examined for antisense activity (molecules that bind to complementary RNA) and more recently antigene activity (molecules that directly bind to DNA). PNA displays excellent activity as both an antisense and antigene molecule. Incorporation of cyclopentane units into PNA increases binding to complementary DNA and RNA, so cyclopentane-modified PNA should further improve the activity of PNA in either capacity. PNAs targeted to the DNA region of a protein called P-gp, a protein known to promote efflux of chemotherapeutic drugs in cancer cells. This protein is often found in multi-drug resistant cancers. Elimination of this protein can restore chemical sensitivity of these cancers, making chemotherapy a viable option to treat these cancers. Regular and cyclopentane-modified PNA that target a site of DNA on the P-gp gene were prepared and the initial results show that cyclopentane-modified PNA is more successful at repressing the expression of the protein than the regular, unmodified PNA.

Isothermal Temperature Control Experiment.

Figure 6:
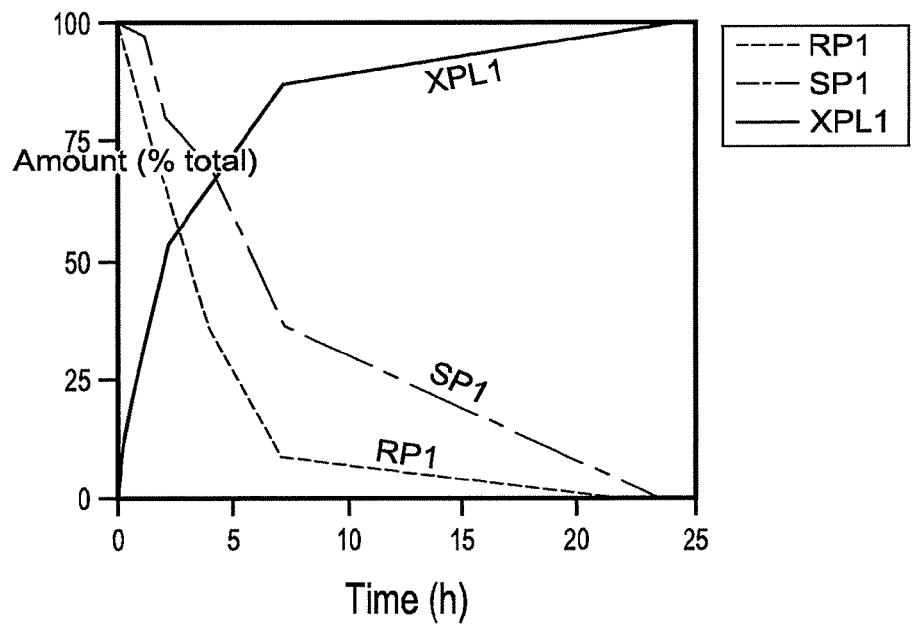
FIG. 6 presents results from an isothermal temperature control experiment. Synthetic Target DNA: 5'-GGA-TTA-TTG-TTA-TAG-GAA-TAG-TTA-AAT-3; (SEQ ID NO:9); Surface Probe (SP1) H$_2$NCO-Lys-(mPEG-Cys-Ac)-TTA-TAA-CTA-TTC-CTA-mPEG$_2$-Ac (SEQ ID NO:10); Reporter Probe (RP1): H$_2$NCO-Lys-(mPEG-Ac)-CCT-AAT-AAC-AAT-mPEG$_5$-Mal (SEQ ID NO:11).

A DNA detection experiment was run using the following components: Synthetic Target DNA: 5'-GGA-TTA-TTG-TTA-TAG-GAA-TAG-TTA-AAT-3' (SEQ ID NO. 9); Surface Probe (SP1): $H_2$NCO-Lys-(mPEG-Cys-Ac)-TTA-TAA-CTA-TTC-CTA-mPEG$_2$-Ac (SEQ ID NO:10); Reporter Probe (RP1): $H_2$NCO-Lys-(mPEG-Ac)-CCT-AAT-AAC-AAT-mPEG$_5$-Mal (SEQ ID NO:11). Probes synthesized using Boc- or Fmoc-SPPS as indicated; DNA purchased from commercial vendor. Conditions were 10 μM PNA (equimolar DNA where noted) 1×PBS, 1 μM EDTA, and pH=7.2. A plot of amount of SP1, RP1 and XPL1 (cross-linked product) versus time is presented in FIG. 6.

Immobilized PNA/DNA Sandwich Hybridization and Capture.

Figure 7:
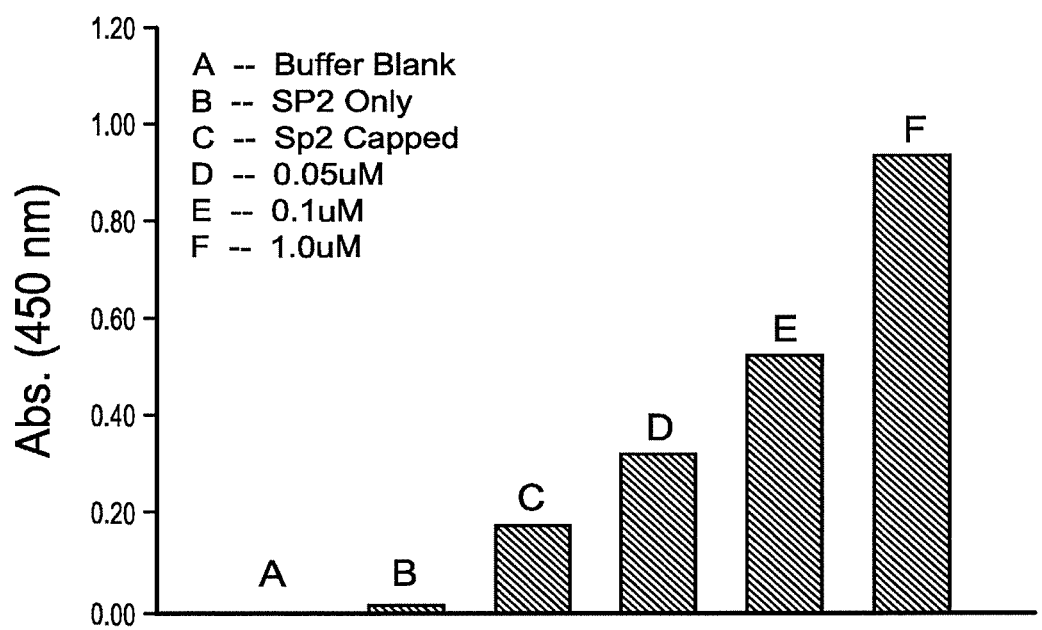
FIG. 7 presents results from immobilized PNA/DNA sandwich hybridization and capture experiments.

A DNA detection experiment was run using the following components: Synthetic Target DNA: 5'-GGA-TTA-TTG-TTA-TAG-GAA-TAG-TTA-AAT-3' (Boc-based) (SEQ ID NO. 9), Surface Probe (SP2): $H_2$NCO-Lys-(mPEG-X)-TTA-TAA-CTA-TTC-CTA-mPEG-$NH_2$ (SEQ ID NO:10), where X is —(C=O)$CH_2CH_2$SH, Reporter Probe (RP2): $H_2$NCO-Lys-(mPEG-BT)-CCT-AAT-AAC-AAT-mPEG$_5$-Mal (Fmoc-based) (SEQ ID NO:11) were utilized. Conditions were as follows: PNA/DNA conc. as indicated; 2× hot washes; followed by 3× washes with 10 mM $NaH_2PO_4$, 0.1 mM EDTA, 0.05% TWEEN 20, pH 7.5 (RT), then 3×50 mM $Na_2HPO_4$, 100 mM NaCl, pH 7.0 (RT); HRP (0.25 ug/mL) incubated 20 min in well; TMB incubated 7 min. ESI-MS [M+Na]+, calc'd −8859.7, obs'd −8860.0. Results are presented in FIG. 7.

XPL Surface Experiments.

Figure 8:
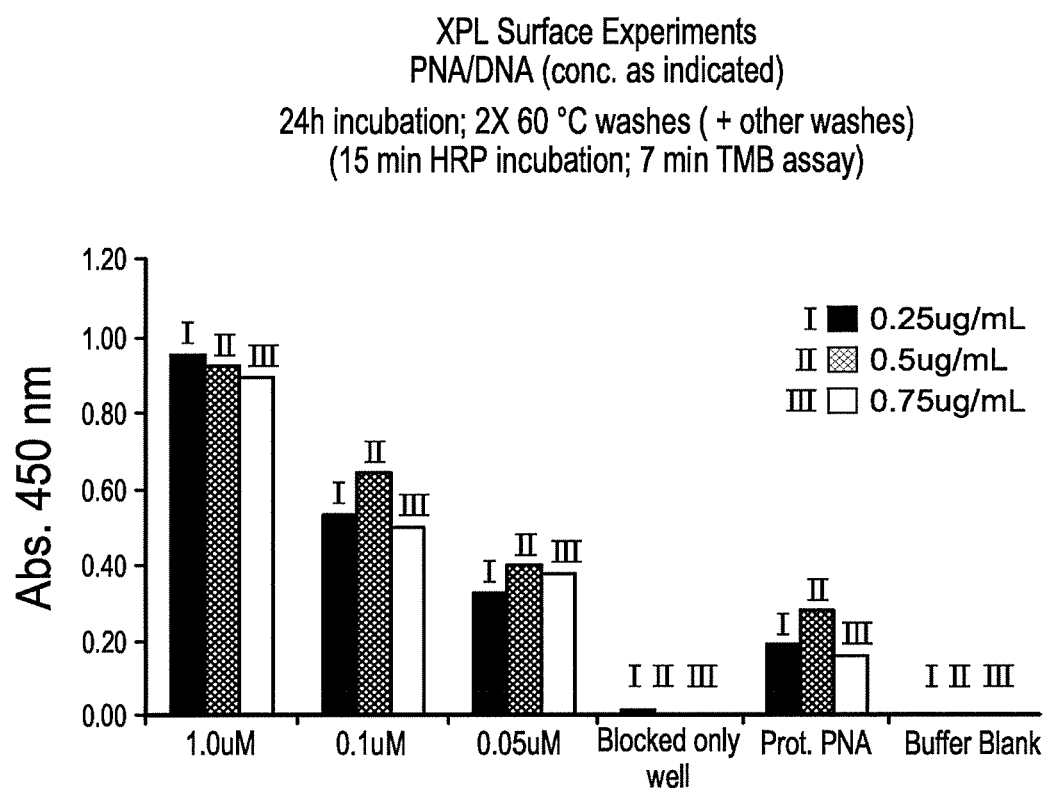
FIG. 8 presents results from experiments using different DNA concentrations.

Results from DNA detection experiments using 0.05, 0.1, and 1.0 μM DNA are presented in FIG. 8. Additional measurements were made with a blocked only well, a buffer blank, and prot. PNA. Results of absorbance at 450 nm versus PNA concentration for 0.05, 0.1, and 1.0 μM DNA experiments are shown in the bar graph.

As used herein, the terms "a", "an", "the" and the like refer to both the singular and plural unless the context clearly indicates otherwise.

Also as used herein, the description of one or more method steps does not preclude the presence of additional method steps before or after the combined recited steps. Additional steps may also be intervening steps to those described. In addition, it is understood that the lettering or order of process steps or ingredients is a convenient means for identifying discrete activities or ingredients and the recited lettering can be arranged in any reasonable sequence.

Where a range of numbers is presented in the application, it is understood that the range includes all integers and fractions thereof between the stated range limits. A range of numbers expressly includes numbers less than the stated endpoints and those in-between the stated range. A range of from 1-3, for example, includes the integers one, two, and three as well as any fractions that reside between these integers.

What is claimed:

1. A method for lowering the detection limit in a method of detecting a nucleic acid of interest in a solution, the method comprising:
   (a) contacting the solution with a PNA capture probe and a PNA reporter probe; wherein
      (i) the PNA capture probe comprises at least one trans-cyclopentane residue and the PNA capture probe is attached to a surface;
      (ii) the PNA reporter probe consists of a sequence that is complementary to a portion of the nucleic acid of interest and two linker-attached biotins; and
      (iii) the PNA capture probe and the PNA reporter probe each comprise a nucleobase sequence that is complementary to different portions of the nucleic acid of interest;
   (b) forming a complex of the PNA capture probe, PNA reporter probe, and nucleic acid of interest,
   (c) contacting the complex with a colorimetric detection system to obtain a color signal characteristic of bound biotin,
   (d) determining the presence or absence of the nucleic acid of interest from the color signal obtained in step (c);
   wherein the lower level of detection of the method is $10^{-20}$ moles of the nucleic acid of interest.

2. The method of claim 1, wherein the surface is visually observed to detect the appearance of a detectable signal from the reporter probe.

3. The method of claim 1, wherein the surface is visually observed to detect the appearance of color from the reporter probe.

4. The method of claim 1, wherein the surface is washed prior to determining the presence of the reporter molecule.

5. The method of claim 1, wherein the nucleic acid of interest is a nucleic acid present in anthrax, avian flu, tuberculosis, severe acute respiratory syndrome (SARS), human papilloma virus (HPV), or human immunodeficiency virus (HIV).

6. The method of claim 1, wherein the nucleic acid of interest is anthrax DNA.

7. The method of claim 1, wherein the nucleic acid of interest is HIV-1 RNA.

8. The method of claim 1, wherein the PNA capture probe comprises more than one trans-cylcopentane residues.

9. The method of claim 1, wherein the sequence of the PNA reporter probe comprises at least one trans-cyclopentane residue.

10. The method of claim 1, wherein the colorimetric detection system comprises incubation of step (a) product with avian-horseradish peroxidase conjugate followed by detection with tetramethylbenzidine.

11. The method of claim 10, wherein the avidin-horseradish peroxidase conjugate is a poly-horseradish peroxidase-avidin conjugate.

12. A kit for detecting a target nucleic acid, said kit having a sensitivity of detection of $10^{-20}$ moles of the target nucleic acid in a test sample; the kit comprising a PNA capture probe and a PNA reporter probe; wherein
  (i) the PNA capture probe comprises at least one trans-cyclopentane residue, the PNA capture probe is attached to a surface;
  (ii) the PNA reporter probe consists of a sequence that is complementary to a portion of the nucleic acid of interest and two linker-attached biotins and the PNA reporter probe is capable of being detected by a colorimetric detection system for biotin; and
  (iii) the PNA capture probe and the PNA reporter probe each comprise a nucleobase sequence that is complementary to different portions of the nucleic acid of interest.

13. The kit of claim 12, further comprising horseradish peroxidase (HRP)-streptavidin.

14. The kit of claim 12, further comprising a wash solution.

15. The kit of claim 12, additionally comprising instructions for visually detecting the presence of the target nucleic acid.

16. A detection assay for detecting the presence of a target nucleic acid, the detection assay comprising:
  (a) a reaction zone comprising a solution and
  (b) a surface defining at least a portion of the reaction zone, wherein the reaction zone comprises:
    (i) PNA capture probe for the target nucleic acid, the PNA capture probe comprising at least one trans-cyclopentane residue, the PNA capture probe is attached to a surface; and
    (ii) PNA reporter probe for the target nucleic acid, the PNA reporter probe in the solution; the PNA reporter probe consists of a sequence that is complementary to a portion of the nucleic acid of interest and two linker-attached biotins;
  the PNA capture probe and the PNA reporter probe are complementary to different portions of a target nucleic acid; and
  wherein the nucleic acid of interest is detected by observance of a color signal generated by a colorimetric detection system for bound biotin when $10^{-20}$ moles of the nucleic acid of interest are present in the solution by contacting the target nucleic acid with the PNA reporter probe and the PNA capture probe and determining the presence of the nucleic acid of interest by detecting the presence of a complex between target nucleic acid, the PNA capture probe and the PNA reporter probe attached to the surface.

17. The method of claim 16, wherein the avidin-horseradish peroxidase conjugate is a poly-horseradish peroxidase-avidin conjugate.

\* \* \* \* \*

SEQUENCE LISTING

```
<160> NUMBER OF SEQ ID NOS: 11

<210> SEQ ID NO 1
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 1
ggattattgt taaatattga taaggat                                         27

<210> SEQ ID NO 2
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 2
ggattattgt taaatattgg taaggat                                         27

<210> SEQ ID NO 3
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 3
```
ggattattgt taaatattgc taaggat                                               27

<210> SEQ ID NO 4
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 4
ggattattgt taaatattgt taaggat                                               27

<210> SEQ ID NO 5
<211> LENGTH: 15
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(1)
<223> OTHER INFORMATION: egl = 8-amino-3,6-dioxaoctanoic acid
<220> FEATURE:
<221> NAME/KEY: misc_feature
<222> LOCATION: (15)..(15)
<223> OTHER INFORMATION: CONH2

<400> SEQUENCE: 5
atccttatca ataat                                                           15

<210> SEQ ID NO 6
<211> LENGTH: 15
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(1)
<223> OTHER INFORMATION: egl = 8-amino-3,6-dioxaoctanoic acid
<220> FEATURE:
<221> NAME/KEY: misc_feature
<222> LOCATION: (8)..(8)
<223> OTHER INFORMATION: tcyp = PNA residue derived from (S,S)-trans-
      1,2-cyclopentane diamine
<220> FEATURE:
<221> NAME/KEY: misc_feature
<222> LOCATION: (15)..(15)
<223> OTHER INFORMATION: CONH2

<400> SEQUENCE: 6
atccttatca atatt                                                           15

<210> SEQ ID NO 7
<211> LENGTH: 12
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (12)..(12)
<223> OTHER INFORMATION: Lys-Lys-CONH2
<220> FEATURE:
<221> NAME/KEY: misc_feature
<222> LOCATION: (12)..(12)
<223> OTHER INFORMATION: egl = 8-amino-3,6-dioxaoctanoic acid; BT =
      biotin

<400> SEQUENCE: 7
taacaataat cc                                                              12

```
<210> SEQ ID NO 8
<211> LENGTH: 12
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (12)..(12)
<223> OTHER INFORMATION: Lys-Lys-Lys-CONH2
<220> FEATURE:
<221> NAME/KEY: misc_feature
<222> LOCATION: (12)..(12)
<223> OTHER INFORMATION: BT = biotin; egl = 8-amino-3,6-dioxaoctanoic
      acid

<400> SEQUENCE: 8
taacaataat cc                                                              12

<210> SEQ ID NO 9
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 9
ggattattgt tataggaata gttaaat                                               27

<210> SEQ ID NO 10
<211> LENGTH: 15
<212> TYPE: DNA
<213> ORGANISM: Artificial Sequence
<220> FEATURE:
<223> OTHER INFORMATION: Oligonucleotide primer

<400> SEQUENCE: 10
ttataactat tccta                                                           15

<210> SEQ ID NO 11
<211> LENGTH: 12
<212> TYPE: DNA
<213> ORGANISM: Artificial Sequence
<220> FEATURE:
<223> OTHER INFORMATION: Oligonucleotide primer

<400> SEQUENCE: 11
cctaataaca at                                                              12
```